United States Patent [19]

Kelly et al.

[11] Patent Number: 5,385,654

[45] Date of Patent: Jan. 31, 1995

[54] CONTROLLED TEMPERATURE ANION SEPARATION BY CAPILLARY ELECTROPHORESIS

[75] Inventors: Lenore Kelly, Sunnyvale; Dean S. Burgi, Menlo Park; Robert J. Nelson, Fremont, all of Calif.

[73] Assignee: Thermo Separation Products Inc., Fremont, Calif.

[21] Appl. No.: 88,439

[22] Filed: Jul. 7, 1993

[51] Int. Cl.⁶ .................. G01N 27/26; G01N 27/447
[52] U.S. Cl. ............................ 204/180.1; 204/299 R
[58] Field of Search ...................... 204/299 R, 180.1

[56] References Cited

U.S. PATENT DOCUMENTS

| | | | |
|---|---|---|---|
| 3,932,264 | 1/1976 | Haruki et al. | 204/299 R |
| 3,941,678 | 3/1976 | Akiyama | 204/299 R |
| 5,066,382 | 11/1991 | Weinberger et al. | 204/299 R |
| 5,104,506 | 4/1992 | Jones et al. | 204/180.1 |
| 5,128,005 | 7/1992 | Jones et al. | 204/180.1 |
| 5,156,724 | 10/1992 | Jones et al. | 204/180.1 |
| 5,167,827 | 12/1992 | Glatz | 210/656 |
| 5,240,576 | 8/1993 | Lauer | 204/180.1 |

OTHER PUBLICATIONS

Small et al, "Indirect Photometric Chromatography," American Chem. Soc. 1982.
Foret et al, "Indirect Photometric Detection in Capillary Zone Electrophoresis," Elsevier Science Publishers B.V. 1989.
Kelly et al, "Separation of Small Anions Using Dichromate for Indirect UV Detection", Research Disclosure, Aug. 1992.
L. Kelly, "Separation of Organic Acids Using Phthalate Ion for Indirect UV Detection," publ. in Research Disclosure, Aug. 10, 1993.
L. Kelly et al, "Capillary Zone Electrophoresis of Organic Acids and Anions," J. of Liq. Chrom., vol. 16, Nos. 9 & 10, pp. 2103-2122 1993.
P. Mortin, M. B. Amram, S. Favier, R. Heimburger, and M. Leroy "Separation of arsenic anions by capillary zone electrophoresis with UV detection" Fresenius' Journal of Chemistry 342 (1992) 357–362.
Yasuyuki Kurosu, Kiyokatsu Hibi, Toru Sasaki, and Muneo Saito, "Influence of Temperature Control in Capillary Electrophoresis" Journal of High Resolution Chromatography vol. 14 (1991) 200–203.

Primary Examiner—John Niebling
Assistant Examiner—John S. Starsiak, Jr.
Attorney, Agent, or Firm—Killworth, Gottman, Hagan & Schaeff

[57] ABSTRACT

An improved method for the separation of anions using capillary electrophoresis techniques. Both organic and inorganic anions may be separated. Using precise control of the temperature of the fluid in the capillary column; the migration speed and order of migration of the anions may be controlled to improve the selectivity of the process. Further, close temperature control provides a high degree of repeatability for samples and enables one to track and identify specific anions.

18 Claims, 10 Drawing Sheets

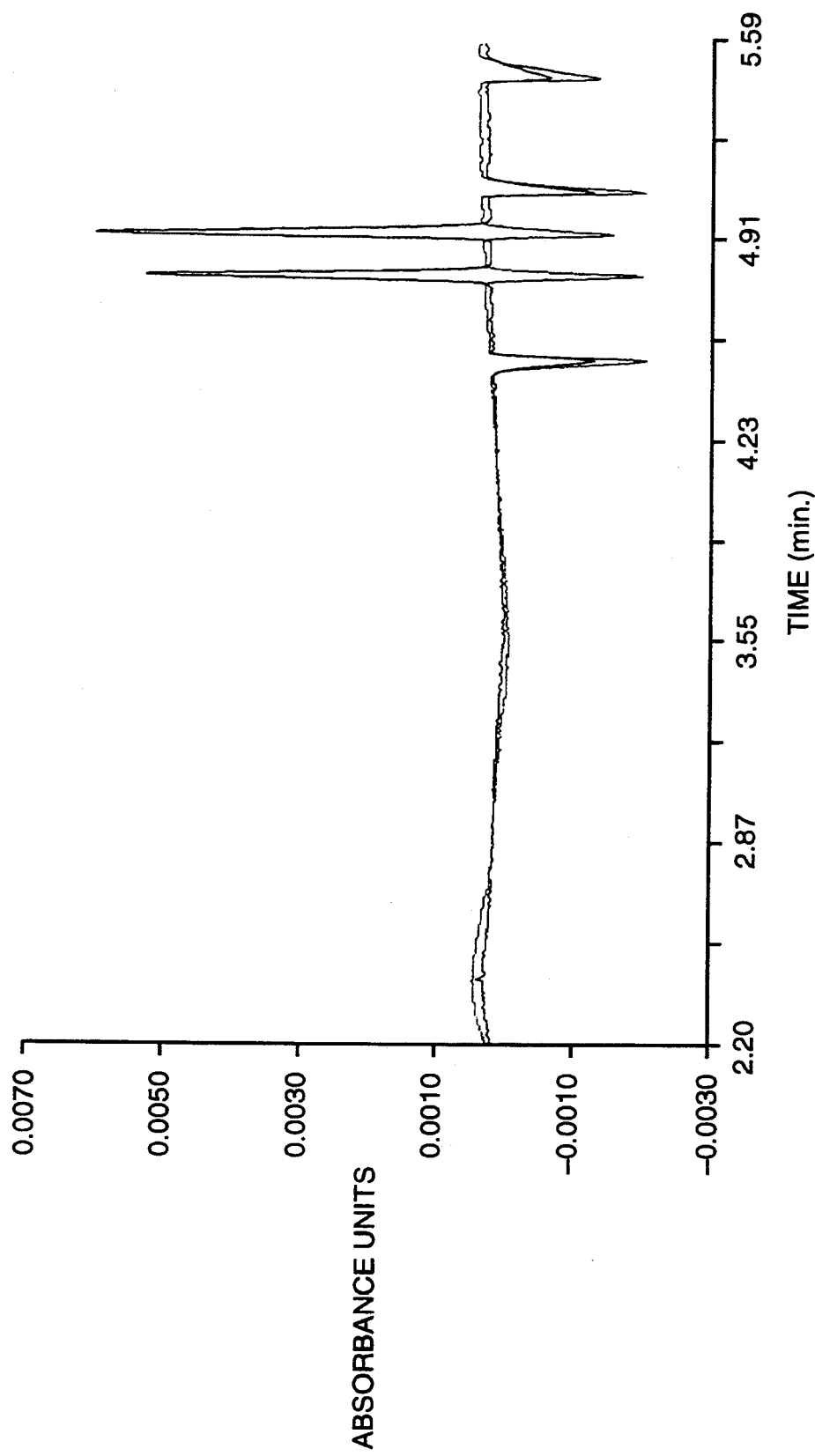

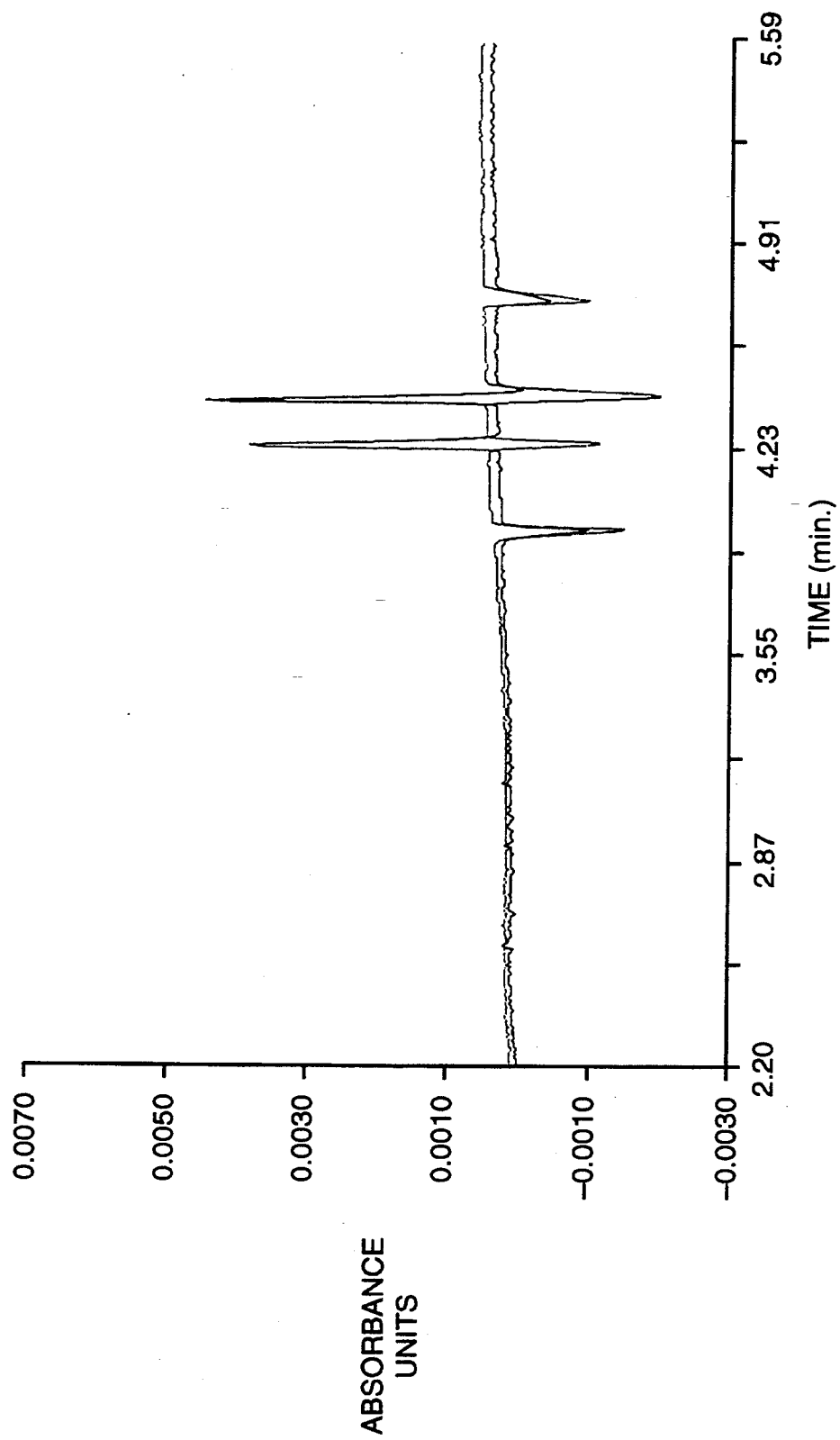

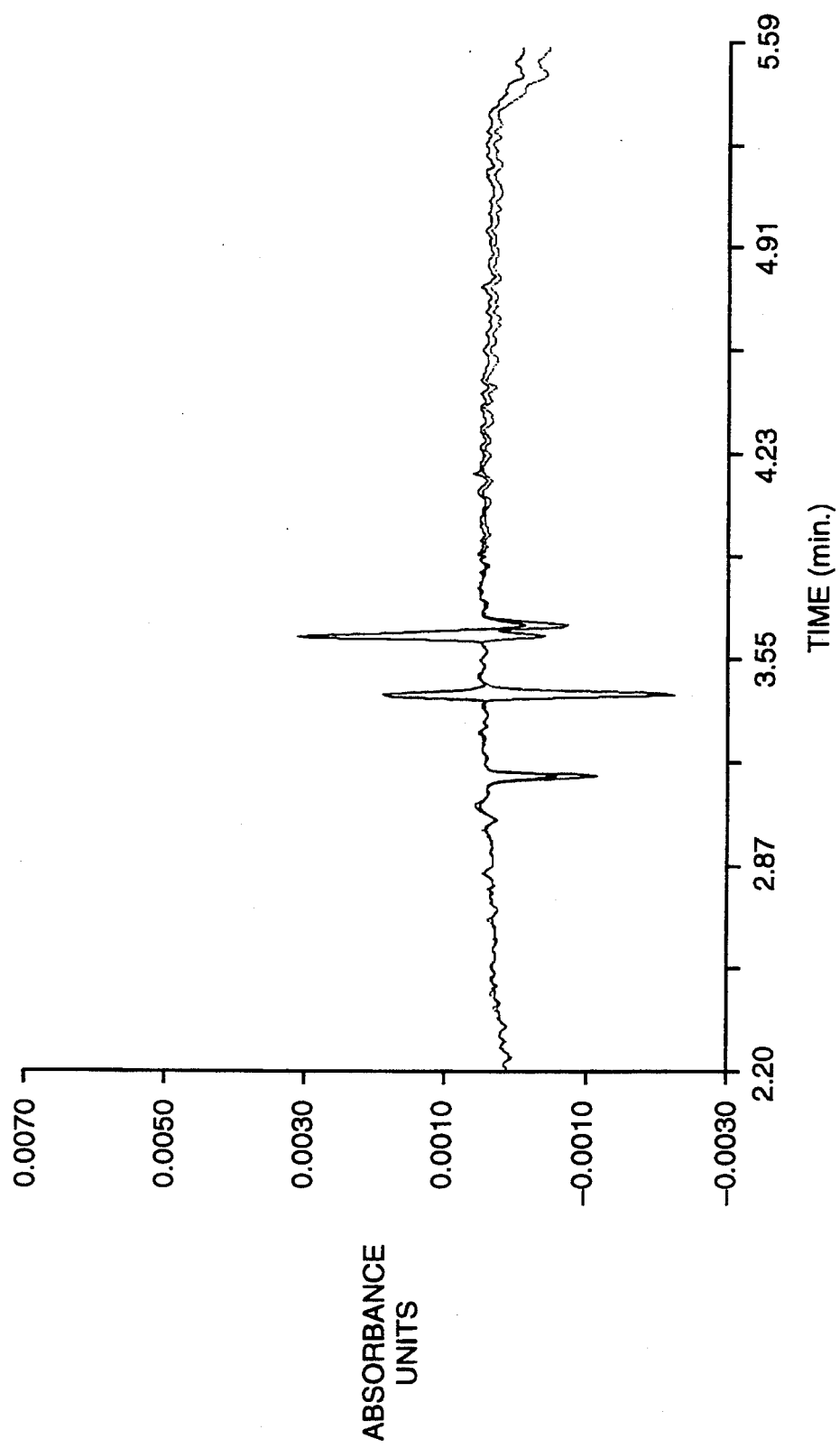

CONTROLLED TEMPERATURE ANION SEPARATION BY CAPILLARY ELECTROPHORESIS

BACKGROUND OF THE INVENTION

The present invention relates to the separation and detection of common anionic species using capillary electrophoresis, and more particularly to the use of temperature control in a capillary electrophoresis system to improve separation and reproducibility for the detection of such anionic species.

The separation and/or detection of ionic species in chemical analysis is generally carried out using the electrochemical properties of the analytes. These properties may include ionic interactions and conductivity in ion chromatography and ionic mobility in capillary electrophoresis. Capillary zone electrophoresis (CZE) is a powerful and efficient method to separate small analytes at very low concentration levels by exploiting the different mobilities of sample components in an electric field.

A conventional CZE system typically includes a buffer-filled capillary column with inlet and outlet ends disposed into two reservoirs. The buffer is generally an electrically conductive medium, sometimes termed the "carrier electrolyte". The system also includes means for introducing the sample into the capillary column, an on-column detector for sensing the sample zones as they pass the detector, and a high voltage source to apply a voltage to the capillary column to cause migration and separation of the sample into identifiable components. The ionic species in the sample move from one electrode toward the other in the capillary column at a rate which is dependent, inter alia, upon the electrical charge, molecular size, mobility of those ions, and/or field strength.

However, many analytes, including most inorganic ions, do not absorb ultraviolet or visible light. As capillary electrophoresis systems generally use direct photometric techniques such as ultraviolet/visible light (UV-VIS) detectors, the ions pass by the detector without being observed. These ions can be detected, however, using the technique of indirect photometric detection. Indirect photometric detection relies on the presence of light-absorbing buffer electrolyte ions in the sample. It is the absorbance of these buffer electrolytes which is monitored by the detector, not the absorptivity that the sample components may display.

Because the solution in the capillary is constrained to remain electrically neutral, sample ions displace the light-absorbing buffer electrolyte ions on a charge-for-charge basis as the sample migrates through the capillary. As the buffer electrolyte ions are displaced by the sample ions, more photons pass through to the detector. This increase in light throughput is recorded by the detector as a decrease in absorbance and is characterized by a negative peak. The magnitude of the negative peak is dependent upon the concentration of the displacing ion, the ratio of the negative charges on the buffer electrolyte ion to the sample ion, and finally, the concentration and extinction coefficient of the buffer electrolyte. Thus, non-absorbing ion species in the sample can be detected, and their concentrations determined using this technique.

Methods using indirect photometric detection in capillary electrophoresis have been described in the published literature, for example, by Foret et al., *J. Chromatography*, 470:299–308 (1989), and Kuhr et al., *Anal. Chem.*, 60:2642–2646 (1988) and 60:1832–1844 (1988). Jones et al., U.S. Pat. Nos. 5,104,506, 5,128,005, and 5,156,724, also describe the use of indirect photometric techniques for the separation and detection of samples containing mixtures of common ionic species. However, problems remain in attempting to resolve and identify certain ion mixtures because some ions have similar migration rates and transparency to or absorbance of ultraviolet light.

To improve sensitivities for detection of certain ions below concentrations of about 1 ppm, other techniques such as electrokinetic injection, the use of electroosmotic flow modifiers, and changes in pH have been used. However, the need still exists in the art for improved methods in detection techniques in capillary electrophoresis, both to improve the separation and detection of very small concentrations of ion species, especially those which are nonabsorbers of light.

SUMMARY OF THE INVENTION

The present invention meets those needs by providing an improved method for the separation of anions using capillary electrophoresis techniques. Both organic and inorganic anions may be separated. Using precise control of the temperature of the fluid in the capillary column, the migration speed and order of migration of the anions may be controlled to improve the selectivity of the process. Because the viscosity of the electrolyte solution in which the sample ions migrate is influenced by temperature, close temperature control provides a high degree of reproducibility for samples and enables one to track and identify specific anions.

In accordance with one aspect of the present invention, a method for detecting and separating anions in a sample using capillary electrophoresis is provided and includes the steps of providing a capillary filled with a negatively-charged carrier electrolyte, heating or cooling the capillary to a target temperature different from ambient temperature, introducing a sample containing one or more anions into the capillary, applying an electrical current to the capillary under conditions causing anions in the sample to migrate and separate, and detecting the anions while maintaining the temperature in the capillary to within ±0.5° C. of the target temperature. Detection of the anions may be by direct or indirect techniques. For example, the anions may be detected by a conductivity detector or a mass spectrometer, or by indirect techniques using a UV/visible detector. In a preferred embodiment of the invention, the carrier electrolyte contains a light-absorbing co-anion, and the anions are detected indirectly using a photometric detector By "carrier electrolyte" or "buffer", we mean any electrically conductive fluid medium for the sample. By "light-absorbing co-anion", we mean salts of anionic species known in this art to absorb visible or ultraviolet light including, but not limited to, chromate, vanadate, phthalate, pyromellitate, benzoate, and singly or multiply-charged carboxylate salts.

The method of the present invention may also be carried out by including an electroosmotic flow modifier in the carrier electrolyte which controls the speed and/or direction of the electroosmotic flow of the carrier electrolyte. While there are many electroosmotic flow modifiers known in the art, for use in this invention, preferred electroosmotic flow modifiers include diethylenetriamine (DETA) and aliphatic trimethyl ammonium halides or hydroxides such as tetradecyltrimethylammonium bromide (TTAB).

The present invention is particularly suited to detect such common low molecular weight inorganic and organic anions such as chloride, nitrate, nitrite, sulfate, and oxalate. Many of these anions have been difficult to detect using conventional CZE techniques in the past because they do not absorb significant amounts of light at many wavelengths in the ultraviolet range. The present invention also provides for the detection of such other common organic anionic species as tartrate, malate, succinate, lactate, acetate, propionate, butyrate, citrate, and caprylate. The use of light-absorbing co-anions in a preferred embodiment which are displaced as the other anions in the sample migrate, permits their presence to be detected as an absence of UV light absorption or a negative peak monitored on the photodetector.

By proper selection of a target temperature which is different from ambient temperature and which may be higher or lower than ambient, and closely controlling the temperature of the fluid in the capillary column to within $\pm 0.5°$ C., and most preferably to within $\pm 0.1°$ C., these anionic species may be separated and detected at very low concentrations of less than 1 ppm, and preferably less than 100 ppb. A preferred target temperature is in the range of from about 25° to 60° C. At a selected temperature within that range, the speed and order of migration, and thus the selectivity of the separation of the anions may be precisely controlled. Further, by programming a temperature increase into the separation process, critical early (negative) peak resolution of fast migrating anions may be preserved while speeding the migration of later (negative) anionic peaks. Thus, both the speed and resolution of the method are enhanced. Additionally, precise temperature control provides a high degree of reproducibility for the process.

In another embodiment of the invention, anions in a sample may be detected by simultaneously monitoring the sample at two different wavelengths with the photodetector. This method takes advantage of the behavior of nitrogen-containing anions such as nitrates, nitrites, and thiocyanates. In this embodiment, the sample is monitored at wavelengths of 210 and 254 nm simultaneously. Nitrate and nitrite strongly absorb at 210 nm, but not at 254 nm. Thus, a strong positive peak occurs at the lower wavelength, while a negative peak is simultaneously observed at the higher wavelength. These unique signatures permit ready identification of nitrogen-containing anions.

In yet another embodiment of the invention, different portions of the same sample are run sequentially, and the temperature in the column for each sample portion is changed. In this manner, the order of elution of the anions in the later sample portions may be compared with the order in the first portion. For example, at a capillary temperature of 20° C., nitrate will elute from the capillary column prior to sulfate. At capillary temperatures of 40° C. and above, that order of elution is reversed and can be observed so that these ions may be readily identified and tracked.

Accordingly, it is a feature of the present invention to provide a method in which improved separation of anions using capillary electrophoresis is accomplished by precise control of the temperature of the capillary column. This, and other features and advantages of the present invention will become apparent from the following detailed description, the accompanying drawings, and the appended claims.

BRIEF DESCRIPTION OF THE DRAWINGS

FIGS. 1A–1E are electropherograms of absorbance units versus time showing the effect of temperature on the separation by capillary electrophoresis of five anions;

DETAILED DESCRIPTION OF THE PREFERRED EMBODIMENTS

Figure 1C:
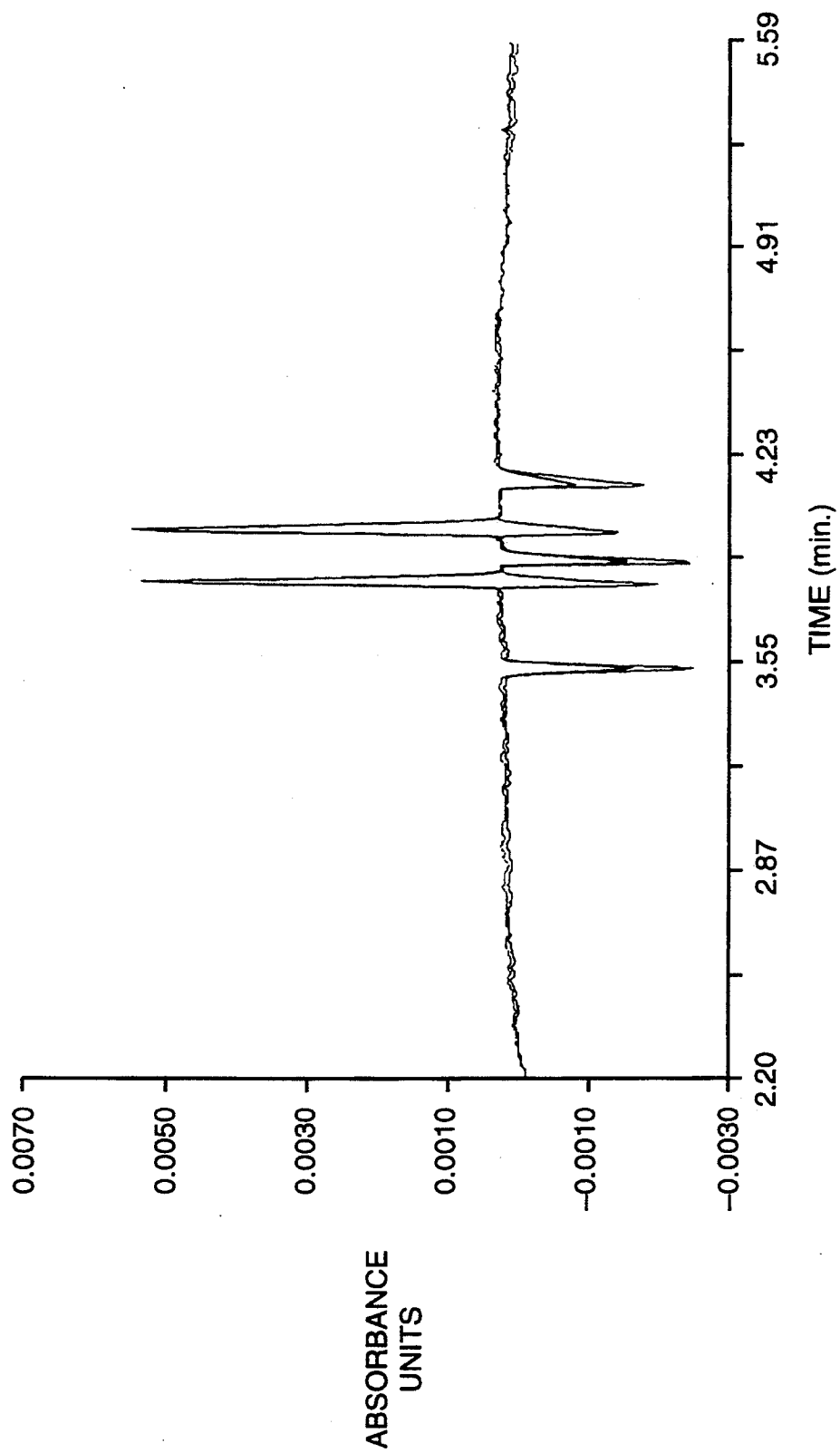
Figure 1E:
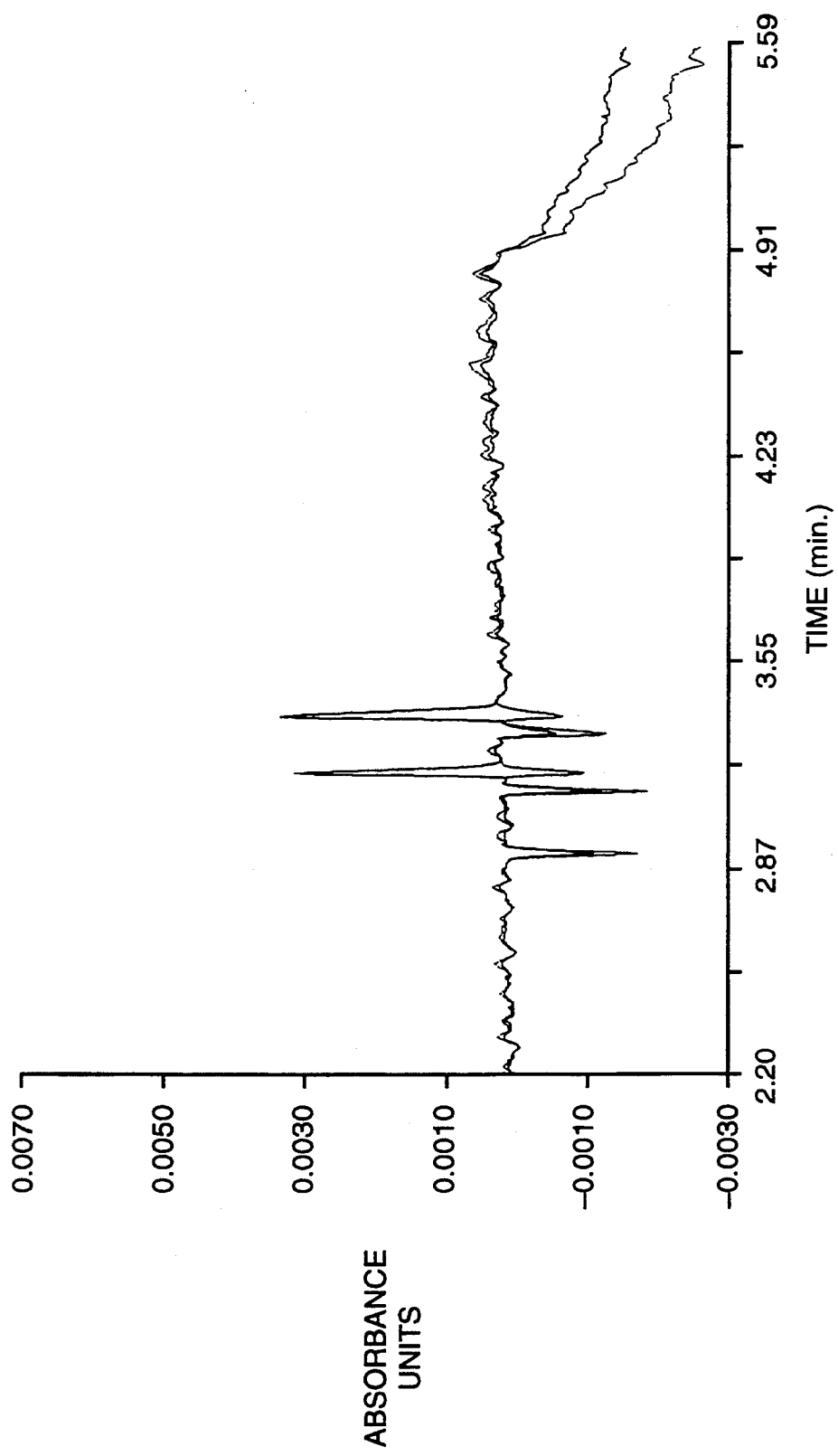

The present invention utilizes capillary electrophoresis in conjunction with precise temperature control to achieve improved separation and detection of common inorganic and organic anionic species. The preferred method of detecting such anions is the use of indirect photometric techniques using a UV/visible detector. For example, Foret et al., *J. Chromatography*, 470:299–308 (1989), describes one procedure for the indirect photometric detection of ions in capillary electrophoresis. In other embodiments of the invention, detection may be accomplished through the use of a conductivity detector or a mass spectrometer.

In a preferred embodiment of the invention using indirect photometric techniques, the process may be carried out manually by filling a capillary tube with a carrier electrolyte containing one or more light-absorbing co-anions of appropriate mobility. Typically, an untreated fused silica capillary tube having a length of 20–120 cm and an internal diameter of between about 25 to 250µ is preferred. The sample containing the anions of interest may then be introduced into the capillary using such standard techniques in the art as hydrostatic pressure, vacuum (hydrodynamic), or electrokinetic injection in which the sample is moved into the capillary by an electrical potential.

After introduction of the sample, the ends of the capillary tube are immersed into liquid-containing reservoirs. The temperature of the capillary tube may be controlled by forced air or liquid circulating around the capillary or by placing the capillary between metal radiator plates. A detector is positioned downstream from the position where the sample is introduced into the capillary, and an electric current is applied to cause the ions in the sample to migrate past the detector. A preferred detector is one which utilizes UV/visible absorbance such as a multiwavelength, scanning UV/VIS detector.

While a manual method may be used, a preferred method for separating and detecting the anions of interest in the present invention is to use an automated capillary electrophoresis instrument such as a SpectraPHORESIS® 1000 system commercially available from Spectra-Physics Analytical, Inc. of Fremont, Calif. Such a system includes an air controlled chamber in which the capillary is maintained at a precisely controlled temperature to within ±0.5° C., and preferably to within ±0.1° C. Operation of the thermal control for such a capillary electrophoresis instrument is described by Weinberger et al. in U.S. Pat. No. 5,066,382, the disclosure of which is hereby incorporated by reference.

The present invention utilizes chemical compounds which facilitate detection of anions in a sample by indirect photometric techniques. Light-absorbing co-anions for use in the practice of the present invention include salts of anionic species known in the art to absorb visible or ultraviolet light. Such salts include chromates, vanadates, phthalates, pyromellitates, benzoates, and singly or multiply-charged carboxylates. For the detection and separation of inorganic anions such as chloride, sulfate, nitrite, and nitrate, preferred salts are potassium dichromate or potassium chromate and salts of 1,2,4,5 benzene tetracarboxylic acid (pyromellitic acid or PMA) having concentrations of from about 10 $\mu$M to 20 mM. For the detection and separation of organic anions such as tartrate, malate, succinate, lactate, acetate, propionate, butyrate, citrate, and caprylate, a preferred salt is potassium hydrogen phthalate having a concentration of from about 1 mM to 10 mM.

The method of the present invention may also be carried out by including an electroosmotic flow modifier in the carrier electrolyte which controls the speed and/or direction of the electroosmotic flow of the carrier electrolyte. While there are many known electroosmotic flow modifiers in the art, preferred electroosmotic flow modifiers for use in this invention include diethylenetriamine (DETA) and aliphatic trimethyl ammonium halides or hydroxides such as tetradecyl-trimethylammonium bromide (TTAB). Preferred concentration ranges are from about 50 $\mu$M to 10 mM.

The present invention is particularly suited to detect such common low molecular weight inorganic and organic anions as chloride, nitrate, nitrite, sulfate, and oxalate. Many of these anions have been difficult to detect using conventional CZE techniques in the past because they do not absorb significant amounts of ultraviolet light. As these smaller anions have high mobilities in the carrier electrolyte, it is preferred that an electroosmotic flow modifier such as DETA be used to suppress (but not reverse) electroosmotic flow. Further, such smaller anions exhibit better peak shapes when the mobility of the light-absorbing co-anion approximates the mobility of such anions.

One preferred ultraviolet light-absorbing co-ion for use in separating and detecting smaller inorganic and organic anions is dichromate. Dichromate has a high mobility in an electric field and approximates the mobilities of the anions of interest. Further, dichromate strongly absorbs ultraviolet light. Another preferred ultraviolet light-absorbing co-ion for use in separating and detecting smaller anions is 1,2,4,5 benzene tetracarboxylic acid (PMA). PMA, with two more carboxylate groups than phthalate has a high mobility due to its higher charge density. We have found that the mobility of PMA is enhanced when the carrier electrolyte is at a pH of 6 or greater, where the acidic carboxylate groups are predominantly ionized.

As is known in this art, increasing the temperature in the capillary decreases the carrier electrolyte solution viscosity. This speeds the migration times of the anions past the detector. However, we have unexpectedly found that temperature also affects the selectivity (i.e., the order of migration) of the separation. Nitrate and nitrite ions migrate with the same relationship to each other, while chloride, sulfate, and oxalate ions also maintain their same relative relationship. However, the nitrogen-containing ions migrate relatively more slowly than the other ions as the temperature in the capillary is increased. Depending upon the target temperature selected, the elution order of the anions may be changed.

By precisely controlling temperature in the capillary, selectivity of the separation, as well as reproducibility, is controlled. The migration times for specific anions is thus predictable and reproducible from run to run to aid in the identification and quantification of such anions. Further, by varying the temperature during a run by increasing it, early peak resolution for highly mobile anions may be maintained while speeding the migration times of later, less mobile anion peaks.

We have also found that simultaneous monitoring by the detector at two different wavelengths provides an additional means of identifying the anions of interest. The nitrogen-containing anions may be distinguished from other anions when absorption is simultaneously monitored at both 210 and 254 nm. For nitrate and nitrite, there is strong absorption at 210 nm but not at 254 nm so that a positive peak is observed at the lower wavelength, but not at the upper wavelength. The presence of positive peaks at 210 nm is thus an identifier of a nitrogen-containing anion in a sample. Additionally, the limits of detection are lower at the shorter wavelength for nitrate and nitrite anions (50 ppb at 210 nm). For other anions such as chloride and sulfate, limits of detection are lower at 254 nm (50 ppb). Thus, by simultaneously monitoring the sample at two different wavelengths, sensitivity of the process is enhanced.

In another embodiment of the invention, organic anions may be separated and detected using the same indirect photometric techniques. A preferred light-absorbing co-anion for use in separating and detecting organic anions is potassium acid phthalate. The use of phthalate as a co-anion in conjunction with an electroosmotic flow modifier such as TTAB, which reverses the electroosmotic flow of the sample, provides good resolution and peak shape of such common organic anions such as tartrate, malate, succinate, lactate, oxalate, acetate, propionate, butyrate, citrate, and caprylate.

In order that the invention may be more readily understood, reference is made to the following examples, which are intended to be illustrative of the invention, but are not intended to be limiting in scope.

Example 1

Detection and separation of several common anions was carried out using capillary electrophoresis with a SpectraPHORESIS®1000 system (Spectra-Physics Analytical, Inc. of Fremont, Calif.). The capillary was untreated, fused silica, 70 cm in length and with a 75$\mu$ internal diameter. A carrier electrolyte solution was prepared as follows. A first stock solution was prepared by dissolving 180 mM potassium dichromate and 1.3 mM H$_2$SO$_4$ in deionized water. A second stock solution was prepared by dissolving boric acid (H$_3$BO$_3$) and sodium tetraborate decahydrate (Na$_2$B$_4$O$_7$·10H$_2$O) in deionized water to a concentration of 2.4M borate; 50 mM of DETA was also added.

The two stock solutions were then combined and diluted in deionized water to a final concentration of 48 mM borate, 1 mM DETA, 1.8 mM dichromate at pH of 8.0. In order to maintain the oxidation state of the dichromate, the stock solutions were not combined until the day of use. Stock solutions of 1000 ppm chloride, nitrate, nitrite, sulfate, and oxalate anions were also prepared by dissolving NaCl, Na$_2$SO$_4$, NaNO$_3$, NaNO$_2$, and H$_2$C$_2$O$_4$·2H$_2$O in deionized water. The anion solutions were diluted as required.

Injection of the sample was carried out using electrokinetic injection for 5 sec at −10 kV. Capillary electrophoresis of individual samples was carried out at −30 kV at temperatures of 20° C. to 60° C., in 10° C. intervals. This operation using a borate buffer produced only a 40μ amp current, permitting enhanced sensitivity for the system. The temperature in the capillary was controlled to within ±0.1° C. of the target temperature for each sample run. The UV/VIS scanning detector on the system was operated to monitor at 210 nm and 254 nm, simultaneously.

As can be seen from FIGS. 1A–1E, the temperature at which the process is carried out is crucial to the selectivity of the separation of the anions. Further, the monitoring of the separation at both 210 nm and 254 nm shows the positive nitrite and nitrate peaks which permits easy identification of these anions. The sulfate-oxalate pair migrates relatively faster than the nitrate-nitrite pair as the temperature is increased. At 20° C., sulfate and oxalate are the last anions to pass the detector. At 30° C. and 50° C. two ions co-elute so that only four peaks are distinguished (at 30° C., nitrate and sulfate co-elute; at 50° C., nitrite and sulfate co-elute). At 60° C., sulfate precedes the nitrogen-containing ions and oxalate appears between them.

The optimal temperature for this separation was 40° C., which takes advantage of both the rapid cycle time and ease of identification of peaks when both 210 nm and 254 nm are monitored.

Example 2

Using the same equipment as in Example 1, the same five anions, chloride, sulfate, nitrate, nitrite, and oxalate, were separated and detected using a carrier electrolyte containing 7 mM PMA as the light-absorbing co-anion, 7 mM sodium hydroxide, and 2 mM DETA at a pH of 9.6. The sodium hydroxide was used to adjust the pH. Mobility of PMA was enhanced at pH 9.6 due to ionization of all carboxylate groups.

Figure 2:
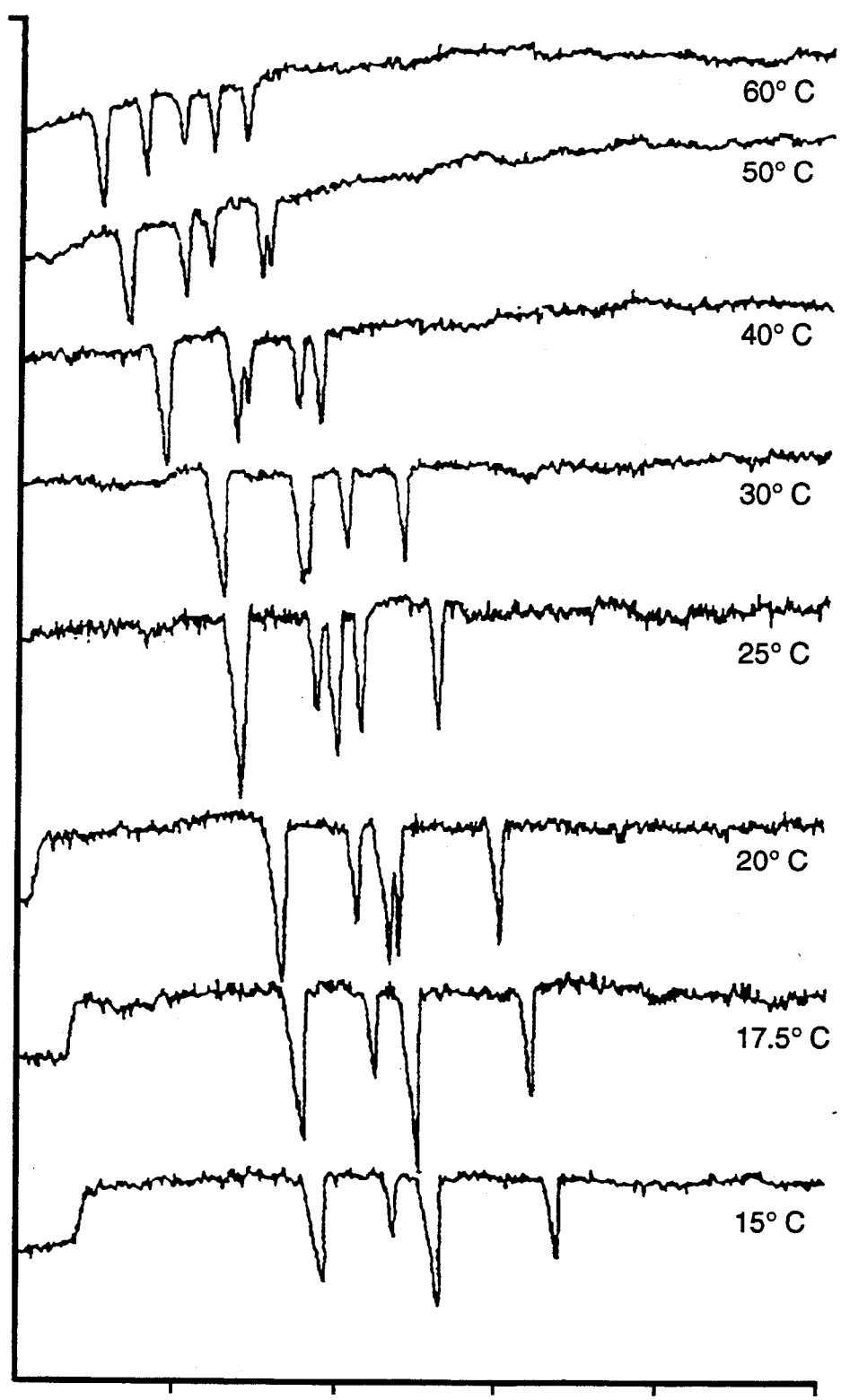
FIG. 2 is a combined electropherogram showing the effect of temperatures ranging from 15° C. to 60° C. on the separation by capillary electrophoresis of five anions.

Sample injection was carried out using electrokinetic injection for 2 sec at −5 kV. Capillary electrophoresis of individual samples was carried out at −25 kV at temperatures of 15° C., 17.5° C., 20° C., 25° C., 30° C., 40° C., 50° C., and 60° C., respectively. The current was less than 40μ amp using a 35cm/50 μm internal diameter untreated, fused silica capillary. The separation was monitored at 254 nm. The results of the separations are shown in FIG. 2.

Again, selectivity of the separation is dependent upon temperature. Nitrite and nitrate ions migrate with the same relationship to each other, while chloride, sulfate, and oxalate also maintain their same relative distances. However, because the nitrogen-containing anions migrate relatively more slowly than the other anions as the temperature is increased, the elution order is a function of the temperature in the capillary. The optimal temperature for this separation using PMA as the UV absorbing co-anion was 60° C. which produced separate, distinct peaks for each anion.

Example 3

Using the same equipment as in Example 1, a number of organic anions were separated and detected. A carrier electrolyte concentrate was prepared by dissolving 50 mM potassium hydrogen phthalate, 5 mM TTAB, and 500 mM 2-(N-morpholino)-ethanesulfonic acid (MES) in deionized water. pH was adjusted to 5.2 using NaOH. When diluted 1:10, the carrier electrolyte had a final concentration of 5 mM phthalate, 0.5 mM TTAB, and 50 mM MES. Stock solutions of 10 ppm organic anions were prepared by dissolving oxalic acid, L-tartaric acid, D,L-malic acid, succinic acid, propionic acid, caprylic acid, and n-butyric acid (sodium salt) in separate deionized water samples.

Figure 3:
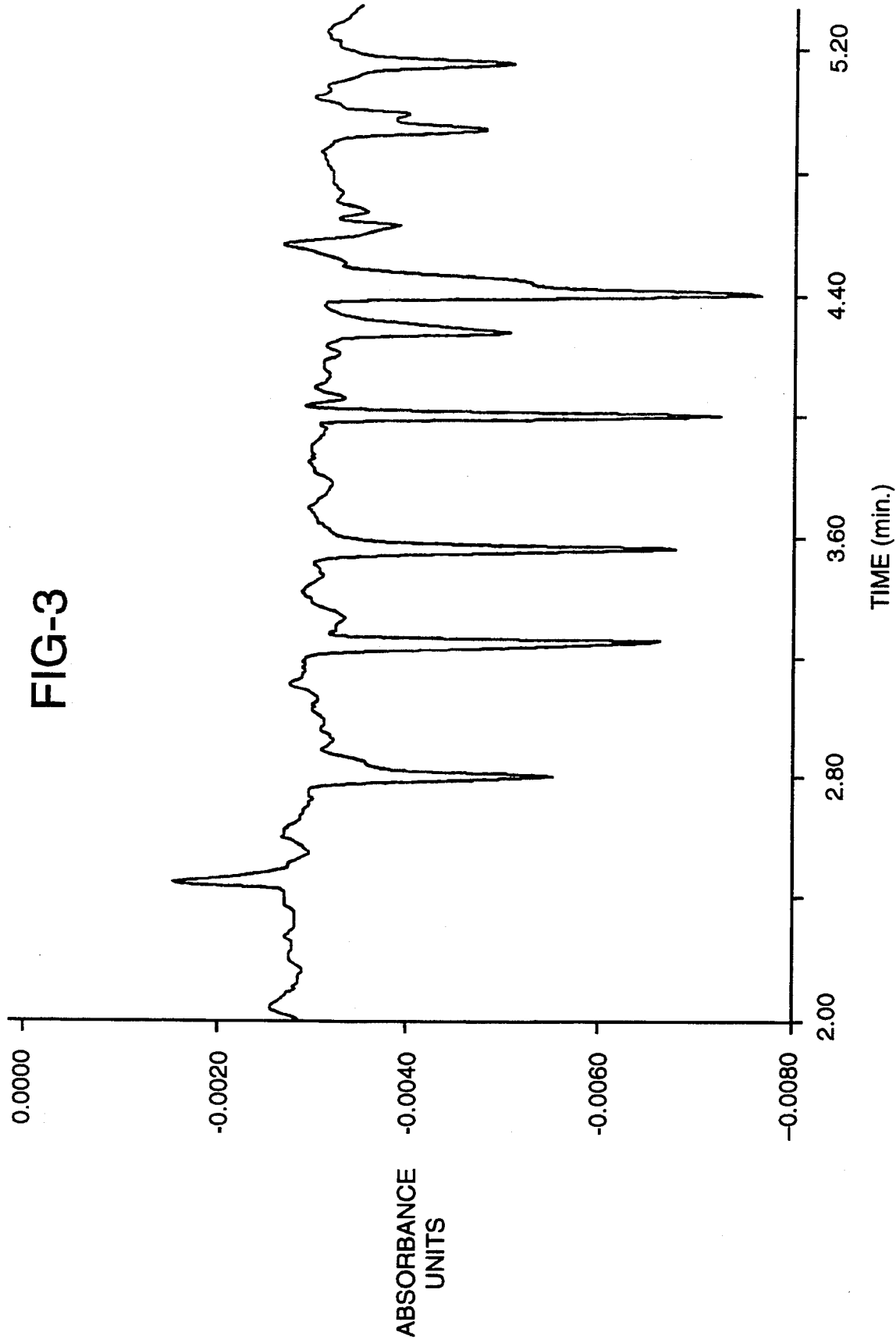
FIG. 3 is an electropherogram of absorbance units versus time for the separation by capillary electrophoresis of eight organic anions.
Figure 4:
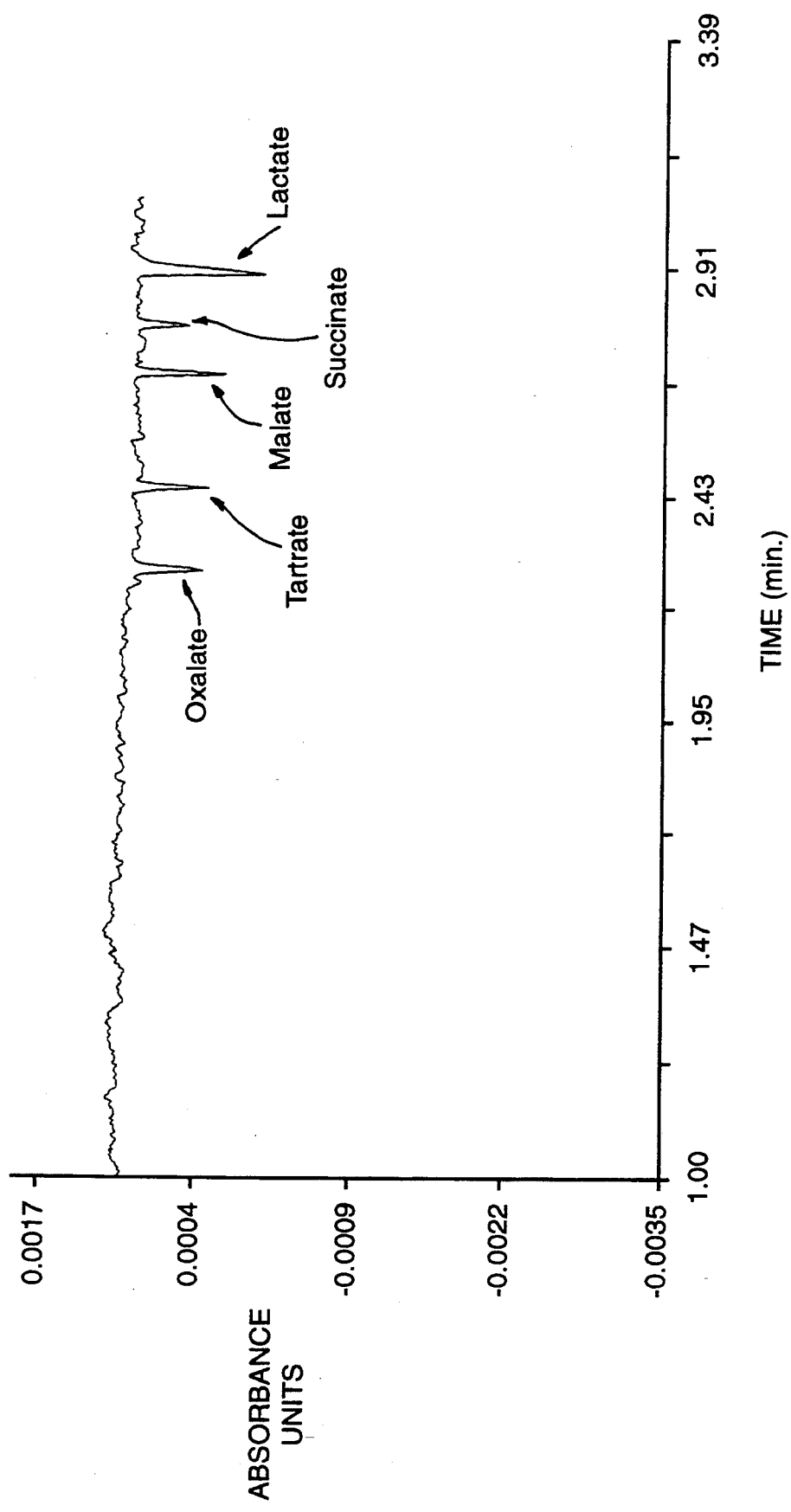
FIG. 4 is an electropherogram of absorbance units versus time for the separation by capillary electrophoresis of five organic anions.

Sample injection was carried out using electrokinetic injection for 1 sec at −10 kV. Capillary electrophoresis of individual samples was carried out at −30 kV at a temperature of 20° C. The current was less than 20μ amp using a 70 cm in length and 75 μm internal diameter untreated, fused silica capillary. The separation was monitored at 205 or 210 nm. The results of the separations, which were run at a pH of 5.0 in the absence of MES, are shown in FIG. 3. The elution order was oxalate, tartrate, malate, succinate, lactate, acetate, propionate, and butyrate. The inclusion of 50 mM of Good's buffer (MES) provided stabilization against pH changes as well as an improved baseline and better peak shape as shown in FIG. 4. The addition of TTAB reversed the electroosmotic flow. The elution order of the anions was: oxalate, tartrate, malate, succinate, and lactate.

Figure 5:
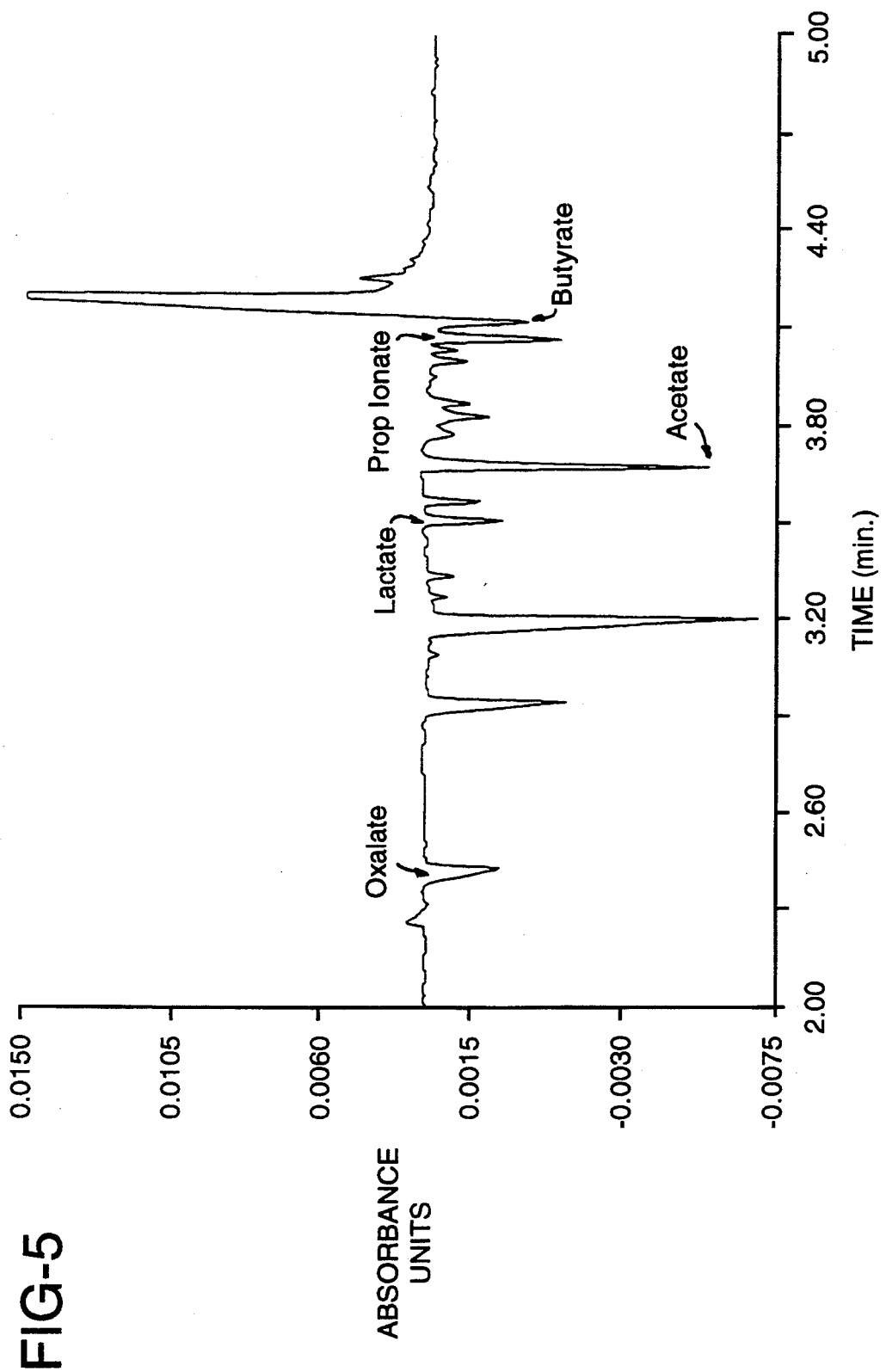
FIG. 5 is an electropherogram of absorbance units versus time for the separation by capillary electrophoresis of organic acids in white wine.
Figure 6:
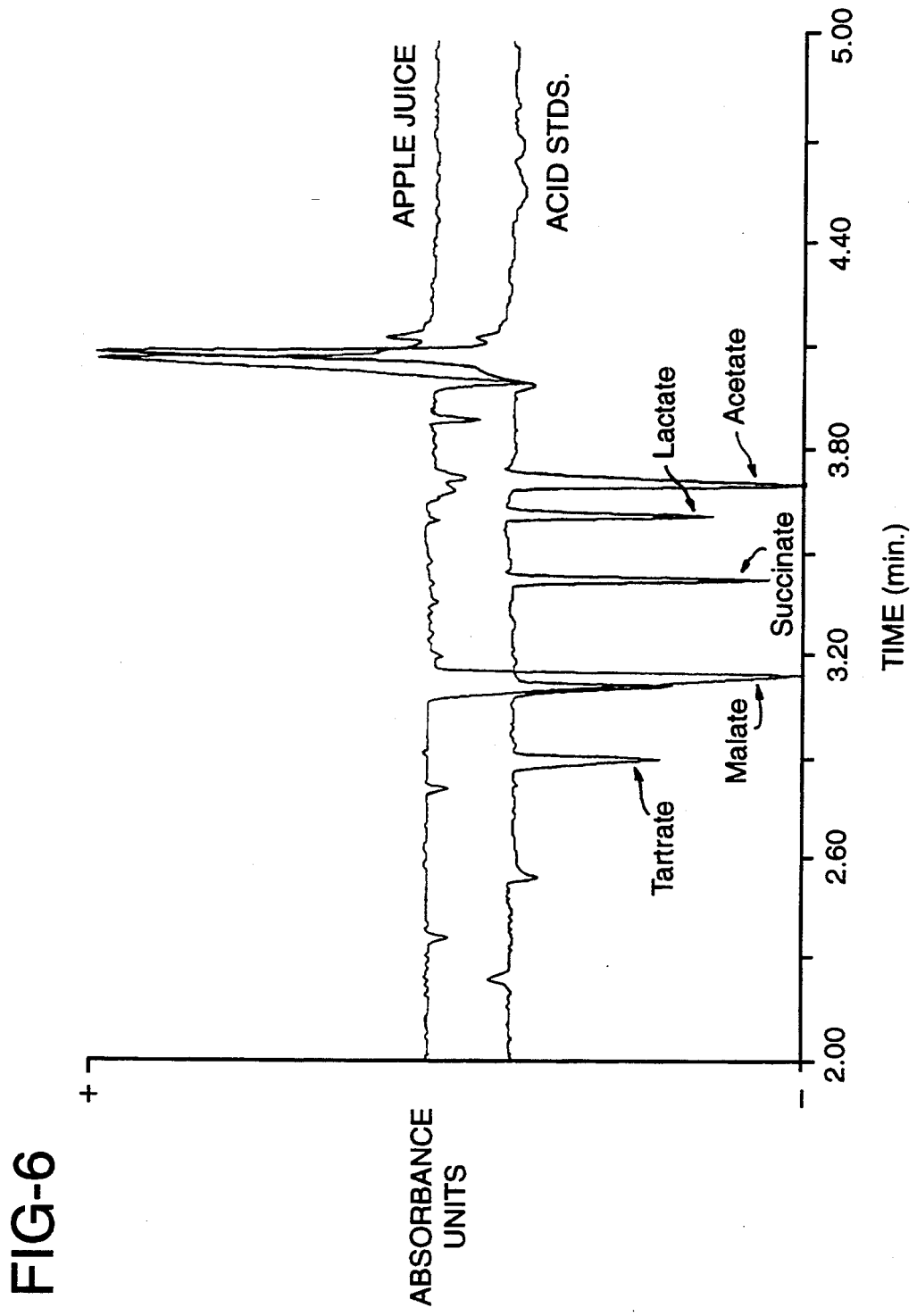
FIG. 6 is an electropherogram of absorbance units versus time for the separation by capillary electrophoresis of organic acids in apple juice run against acids standards to illustrate the reproducibility of the process.

The presence of these organic acids can be detected in beverages such as white wine and apple juice as shown in FIGS. 5 and 6, respectively. Acetate is a major component of this wine as shown in FIG. 5. FIG. 6 also demonstrates the reproducibility of this process run against acids standards as the malate negative peak appears at about 3 min. in both the apple juice and the acids standard.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A method for detecting and separating anions in a sample using capillary electrophoresis comprising the steps of, providing a capillary filled with a carrier electrolyte, said carrier electrolyte containing a light-absorbing co-anion, heating or cooling said capillary to a target temperature in the range of from 25° C. to 60° C., introducing a sample containing one or more anions into said capillary, applying an electrical current to said capillary under conditions causing anions in said sample to migrate and separate, and detecting said anions indirectly using a photometric detector while maintaining the temperature in said capillary to within±0.5° C. of said target temperature, wherein said anions are detected by simultaneously monitoring said sample at two different wavelengths.

2. The method of claim 1 in which said target temperature is 40.° C.

3. The method of claim 1 in which said sample contains one or more anions selected from the group consisting of chloride, nitrate, nitrite, sulfate, and oxalate anions.

4. The method of claim 1 in which said sample is monitored at 205 or 210 and 254 nm simultaneously.

5. The method of claim 1 including the step of including an electroosmotic flow modifier in said carrier electrolyte.

6. The method of claim 5 in which said electroosmotic flow modifier is tetradecyltrimethylammonium bromide.

7. The method of claim 1 in which said sample contains one or more anions selected from the group consisting of oxalate, tartrate, malate, succinate, lactate, propionate, butyrate, citrate, and caprylate.

8. The method of claim 7 including tetradecyltrimethylammonium bromide as an electroosmotic flow modifier.

9. The method of claim 1 in which said light absorbing coanion is selected from the group consisting of pyromellitate, chromate, and dichromate.

10. A method for detecting and separating anions in a sample using capillary electrophoresis comprising the steps of, providing a capillary filled with a carrier electrolyte and diethylenetriamine as an electroosmotic flow modifier, heating or cooling said capillary to a target temperature in the range of from 25° C. to 60° C., introducing a sample containing one or more anions into said capillary, applying an electrical current to said capillary under conditions causing anions in said sample to migrate and separate, and detecting said anions.

11. A method for detecting and separating anions in a sample using capillary electrophoresis comprising the steps of, providing a capillary filled with a carrier electrolyte, heating or cooling said capillary to a target temperature in the range of from 20° to 60° C., introducing a sample containing one or more anions into said capillary, applying an electrical current to said capillary under conditions causing anions in said sample to migrate and separate, and detecting said anions by simultaneously monitoring said sample at two different wavelengths while maintaining the temperature in said capillary to within ±0.5° C. of said target temperature.

12. The method of claim 11 in which said carrier electrolyte contains a light-absorbing co-anion, and said anions are detected indirectly using a photometric detector.

13. The method of claim 12 in which said sample is monitored at 205 or 210 and 254 nm simultaneously.

14. The method of claim 12 in which said light absorbing coanion is selected from the group consisting of pyromellitate, chromate, and dichromate.

15. The method of claim 11 including the step of including an electroosmotic flow modifier in said carrier electrolyte.

16. The method of claim 15 in which said electroosmotic flow modifier is diethylenetriamine.

17. A method for detecting and separating anions in a sample using capillary electrophoresis comprising the steps of, providing a capillary filled with a carrier electrolyte, heating said capillary to a target temperature in the range of from 20° to 60° C., introducing a first portion of a sample containing one or more anions into said capillary, applying an electrical current to said capillary under conditions causing anions in said sample to migrate and separate, detecting said anions by simultaneously monitoring said sample at two different wavelengths, introducing a second portion of said sample into said capillary containing one or more anions, changing said temperature in said capillary, detecting said anions in said second portion, and comparing the order of elution of said anions in said second portion with said first portion.

18. A method for detecting and separating anions in a sample using capillary electrophoresis comprising the steps of, providing a capillary filled with a carrier electrolyte, heating or cooling said capillary to a target temperature in the range of from 25° C. to 60° C., introducing a sample containing one or more anions into said capillary, applying an electrical current to said capillary under conditions causing anions in said sample to migrate and separate, varying said target temperature as said anions migrate, and detecting said anions.

* * * * *

(12) EX PARTE REEXAMINATION CERTIFICATE (7308th)
United States Patent
Kelly et al.

(10) Number: US 5,385,654 C1
(45) Certificate Issued: Jan. 12, 2010

(54) CONTROLLED TEMPERATURE ANION SEPARATION BY CAPILLARY ELECTROPHORESIS

(75) Inventors: Lenore Kelly, Sunnyvale, CA (US); Dean S. Burgi, Menlo Park, CA (US); Robert J. Nelson, Fremont, CA (US)

(73) Assignee: Thermo Separation Products, Inc., Fremont, CA (US)

Reexamination Request:
No. 90/008,000, Jul. 26, 2006

Reexamination Certificate for:
Patent No.: 5,385,654
Issued: Jan. 31, 1995
Appl. No.: 08/088,439
Filed: Jul. 7, 1993

(51) Int. Cl.
*G01N 27/447* (2006.01)

(52) U.S. Cl. ........................................ 204/452; 204/454
(58) Field of Classification Search ........................ None
See application file for complete search history.

(56) References Cited

U.S. PATENT DOCUMENTS

| | | |
|---|---|---|
| 3,616,454 A | 10/1971 | Levy et al. |
| 3,873,432 A | 3/1975 | Israel et al. |
| 4,279,361 A | 7/1981 | Chung |
| 4,486,311 A | 12/1984 | Nakajima et al. |
| 4,708,782 A | 11/1987 | Andresen et al. |
| 4,725,343 A | 2/1988 | Hjerten et al. |
| 4,747,919 A | 5/1988 | Anderson |
| 4,810,456 A | 3/1989 | Bente, III et al. |
| 4,865,706 A | 9/1989 | Karger et al. |
| 4,906,344 A | 3/1990 | Hjerten |
| 4,911,807 A | 3/1990 | Burd |
| 5,073,239 A | 12/1991 | Hjerten |
| 5,085,757 A | 2/1992 | Karger et al. |

OTHER PUBLICATIONS

Spectra Phoresis 1000/500 Field Repair Manual, Spectra Physics Analytical, Part No. A0099–385, 1991.

Grossman, Paul D., Capillary Electrophoresis in Entangled Polymer Solutions, Capillary Electrophoresis, Chapter 8, 1992, pp. 215–233, Academy Press, Inc.

Grossman, Paul D., Factors Affecting the Performance of Capillary Electrophoresis Separations: Joule Heating, Electroosmosis, and Zone Dispersion, Capillary Electrophoresis, 1992, Chapter 1, pp. 3–43, Academy Press, Inc.

Grossman, Paul D., Free–Solution Capillary Electrophoresis, Capillary Electrophoresis, Chapter 4, 1992, p. 111, Academy Press, Inc.

Giese, R. W. et al., Journal of Chromatography, International Journal on Chromatography, Electrophoresis and Related Methods, $1^{st}$ Int. Symp. on High–Performance Capillary Electrophoresis, Oct. 20, 1989, pp. 1–436, vol. 480, Elsevier Science Publishers.

Guttman, Andras et al., Influence of Temperature on the Sieving Effect of Difference Polymer Matrices in Capillary SDS Gel Electrophoresis of Proteins, Analytical Chemistry, Feb. 1, 1993, pp. 199–203, vol. 65, No. 3, American Chemical Society.

Guttman, Andras et al., Capillary Gel Affinity Electrophoresis of DNA Fragments, Analytical Chemistry, Sep. 15, 1991, pp. 2038–2042, vol. 63, No. 18, American Chemical Society.

(Continued)

*Primary Examiner*—Stephen J Stein

(57) ABSTRACT

An improved method for the separation of anions using capillary electrophoresis techniques. Both organic and inorganic anions may be separated. Using precise control of the temperature of the fluid in the capillary column; the migration speed and order of migration of the anions may be controlled to improve the selectivity of the process. Further, close temperature control provides a high degree of repeatability for samples and enables one to track and identify specific anions.

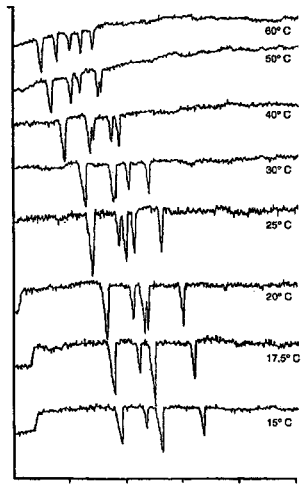

OTHER PUBLICATIONS

Ganzler, Katalin et al., High–Performance Capillary Electrophoresis of SDS–Protein Complexes Using UV–Transparent Polymer Networks, Analytical Chemistry, Nov. 15, 1992, pp. 2665–2671, vol. 64, No. 22, American Chemical Society.

Guttman, Andras et al., Enhanced Separation of DNS Restriction Fragments by Capillary Gel Electrophoresis Using Field Strength Gradients, Analytical Chemistry, Oct. 15, 1992, pp. 2348–2351, vol. 64, No. 20, American Chemical Society.

Cohen, A. S. et al., Rapid separation and purification of oligonucleotides by high–performance capillary gel electrophoresis, Proc. Natl. Acad. Sci. USA, Dec. 1988, pp. 9660–9663, vol. 85.

Guttman, Andras et al., Denaturing capillary gel electrophoreis, Electrophoresis Apparatus, May 1991, pp. 9–10.

Hjerten, S. et al., High–Performance Electrophoresis Of Acidic And Basic Low–Molecular–Weight Compounds And Of Proteins In The Presence Of Polymers And Neutral Surfactants, Journal Of Liquid Chromatography, 1989, pp. 2471–2499, vol. 12(13).

Asakawa, Jun–Ichi, Two–dimensional gel electrophoresis of platelet polypeptides with immobilized pH gradients in capillary tubes, Electrophoresis, 1988, pp. 562–568, vol. 9, VCH Verlagsellschaft mbH, D 6940 Weinheim.

Cobb, Kelly A. et al., High–Sensivity Peptide Mapping by Capillary Zone Electrophoresis and Microcolumn Liquid Chromatography, Using Immobilized Trypsin for Protein Digestion, Analytical Chemistry, Oct. 15, 1989, pp. 2226–2231, vol. 61, No. 20, American Chemical Society.

Schwartz, Herbert C. et al., Analysis of DNA restriction fragments and polymerase chain reaction products towards detection of the AIDS (HIV–1) virus in blood, Journal of Chromatography, 1991, pp. 267–283, vol. 559, Elsevier Science Publishers B V, Amsterdam.

Widhalm, Alexandra et al., Capillary zone electrophoresis with a linear, non–cross–linked polyacrylamide gel: separation of proteins according to molecular mass, Journal of Chromatography, Jul. 19, 1991, pp. 446–451, vol. 549, Nos. 1 and 2, Elsevier Science Publishers.

Sudor, Jan et al., Pressure refilled polyacrylamide columns for the separation of oligonucleotides by capillary electrophoresis, Electrophoresis, 1991, pp. 1056–1058, VCH Verlagsgesselschaft mbH. D–6940 Weinheim.

Bocek, Petr et al., Capillary electrophoresis of DNA in agarose solutions at 40° C., Electrophoresis, 1991, pp. 1059–1061, VCH Verlagsgesellschaft mbH. D–6940 Weinheim.

Burroughs, John A., Size separation of polystryene sulfate particles (189 to 1085 nm radius) in solutions of methy–1–hydroxypropyl–cellulose of different chain lengths, Biochemical and Biophysical Research Communications, Oct. 31, 1991, pp. 1070–1074, vol. 180, No. 2, Academic Press, Inc.

Guszcynski, Tadeusz et al., Electrophoretic separation of S. Pombe chromosomes in polyacrylamide solutions using a constant field, Biochemical and Biophysical Research Communications, Aug. 30, 1991, pp. 482–486, vol. 179, No. 1, Academic Press, Inc.

Strege, Mark et al., Separation of DNA Restriction Fragments by Capillary Electrophoresis Using Coated Fused Silica Capillaries, Analytical Chemistry, Jul. 1, 1991, pp. 1233–1236, vol. 63, No. 13, American Chemical Society.

Hjerten, Stellan, Zone broadening in electrophoresis with special reference to high–performance electrophoresis in capillaries: An interplay between theory and practice, Electrophoresis, 1990, pp. 665–690, VCH Verlagsgesellschaft mbH. D–6940 Weinheim.

Chin, A. Michael et al., Counter–migration capillary electrophoresis (CMCE) in DNA restriction fragment analysis, Dec. 1989, p. 15.

Thormann, Wolfgang et al., Isotachophoretic zone formation of serum albumin in different free fluid electrophoresis instruments, Electrophoresis, 1990, pp. 298–304, VCH Verlagsgesellschaft mbH. D–6940 Weinheim.

Zhu, Mingde et al., Factors Affecting Free Zone Electrophoresis And Isoelectric Focusing In Capillary Electrophoresis, Journal of Chromatography, Oct. 20, 1989, pp. 311–319, vol. 480, Elsevier Science Publishers B V, Amsterdam.

Tanaka, Yoshio et al., Capillary electrophoretic determination of S–carboxymethyl–L–cysteine and its major metabolites in human urine: Feasibility in investigation using on–column detection of non–derivatized solutes in capillaries with minimal electoosmosis, Electrophoresis, 1990, pp. 760–764, VCH Verlagsgesellschaft mbH. D–6940 Weinheim.

Guttman, A. et al., Analytical and Micropreparative Ultrahigh Resolution of Oligonucleotides by Polyacrylamide Gel High–Performance Capillary Electrophoresis, Analytical Chemistry, Jan. 15, 1990, pp. 137–141, vol. 62, No. 2, American Chemical Society.

Orlando, Ron et al., Endothermic Ion–Molecule Reactions: Strategies for Tandem Mass Spectrometric Structural Analyses of Large Biomolecules, Analytical Chemistry, Jan. 15, 1990, pp. 125–129, vol. 62, No. 2, American Chemical Society.

Hershey, Davis, Biochemical Evaluation Of Seiko Chemical Robot DSP–240 For Use With The ABI Model 370A DNA Sequencing System, Jun. 21, 1988, pp. 1–10.

Brehm, G. et al., HPE 100– Capillary Electrophoresis, Zum Titelbild, Jul. 1989, pp. 657–661, GIT Fachz Lab.

Christiansen, L. et al., Separation des proteines, peptides et fragments d'AND par E.C., Dossier Electrophorese Capillaire, Jun. 1990, pp. 35–38, vol. 149, Spectra 2000.

Ouano, A. C., Gel Permeation Chromatogrpahy VII. Molecular Weight Detection Of GPC Effluents, J. Polymer Sci., Symposium No. 43, 1973, pp. 299–310, John Wiley & Sons, Inc.

Takagi, Toshio et al., Application of schlieren optics to real–time monitoring of protein electrophoresis in crosslinker–free linear polyacrylamide solution, Electrophoresis, 1991, pp. 436–438, vol. 12, VCH Verlagsgesellschaft mbH. D–6940 Weinheim.

Grossman, Paul D. et al., Experimental and Theoretical Studies of DNA Separations by Capillary Electrophoresis in Entangles Polymer Solutions, Biopolymers, Sep. 1991, pp. 1221–1228, vol. 31, Issue 10, John Wiley & Sons, Inc.

Bruin, G. J. M. et al., Capillary Zone Electrophoretic Separations Of Proteins In Polyethylene Glycol–Modified Capillaries, Journal of Chromatography, 1989, pp. 429–436, vol. 471, Elsevier Science Publishers B V, Amsterdam.

Chen, A.J.C. et al., Application of High Performance Electrophoresis to DNA Restriction Fragment Analysis, Bulletin 1479, 1989, Bio–Rad Laboratories.

Kasper, Thomas J. et al., Separation And Detection Of DNA By Capillary Electrophoresis, Journal of Chromatography, 1988, pp. 303–312, vol. 458, Elsevier Science Publishers B V, Amsterdam.

Hjerten, Stellan et al., Carrier–Free Zone Electrophoresis, Displacement Electrophoresis And Isolectric Focusing In A High–Performance Electrophoresis Apparatus, Journal of Chromatography, 1987, pp. 47–61, vol. 403, Elsevier Science Publishers B V, Amsterdam.

Guttman, A. et al., Use of Complexing Agents For Selective Separation In High–Performance Capillary Electrophoresis, Journal of Chromatography, 1988, pp. 41–53, vol. 448, Elsevier Science Publishers B V, Amsterdam.

Yamamoto, Hideko et al., Gel Permeation Chromatography Combined With Capillary Electrophoresis For Microanalysis Of Proteins, Journal of Chromatography, 1989, pp. 277–283, vol. 480, Elsevier Science Publishers B V, Amsterdam.

Connell, C. et al., Automated DNA Sequence Analysis, Bio-Techniques, 1987, pp. 342–348, vol. 5, No. 4.

Jovin, T. et al., An Apparatus for Preparative Temperature–Regulated Polyacrylamide Gel Electrophoresis, Analytical Biochemistry, 1964, pp. 351–369, vol. 9.

Hediger, Matthias A., Apparatus and Method for Preparative Gel Electrophoresis, Analytical Biochemistry, 1987, pp. 445–454, vol. 147, Academic Press, Inc.

Novotny, Milos V. et al., Recent advances in capillary electrophoresis of proteins, peptides and amino acids, Electrophoresis, 1990, pp. 735–479, vol. 11, VCH Verlagsgesellschaft mbH. D–6940, Weinheim.

Guttman, Andras et al., Prediction of migration behavior of oligonucleotides in capillary gel electrophoresis, Journal of Chromatography, 1992, pp. 297–303, vol. 593, Elsevier Science Publishers B V, Amsterdam.

Nelson, R.J. et al., Use of Peltier Thermoelectric Devices To Control Column Temperature In High–Performance Capillary Electrophoresis, Journal of Chromatography, 1989, pp. 111–127, Elsevier Science Publishers B V, Amsterdam.

Wehr, Tim, Recent Advances in Capillary Electrophoresis Columns, LC–GC, 1993, pp. 14–20, vol. 11, No. 1, Aster.

Rohlicek, V. et al., Simple device for flushing capillaries in capillary zone electrophoresis, Journal of Chromatography, 1989, pp. 289–291, vol. 480, Elsevier Science Publishers B V, Amsterdam.

Yamamoto, Hideko et al., Capillary Electrophoresis Of Nucleic Acids With A Fully Automated Apparatus, Journal of Chromatography, 1989, pp. 331–338, vol. 480, Elsevier Science Publishers B V, Amsterdam.

Woolley, Paul, Thermal instability of electrophoresis gels, Electrophoresis, 1987, pp. 339–345, vol. 8, VCH Verlagsgesellschaft mbH. D–6940, Weinheim.

Swerdlow et al., Stability of capillary gels for automated sequencing of DNA, Electrophoresis, 1992, pp. 475–483, VCH Verlagsgesellschaft mbH. D–6940, Weinheim.

Vladislav Dolnik et al, Capillary Zone Electrophoresis of Oligonucleotides Factors Affecting Separation, Journal of Chromatograph, 480 (1989) pp. 321–330.

Stellan Hjerten, High–Performance Electrophoresis: The Electrophoretic Counterpart Of High–Performance Liquid Chromatography, Journal of Chromatography, 270 (1983) pp. 1–6.

Spectra Phoresis 1000 Start–Up Guide and Hardware Reference Manual, Spectra Physics, Analytical, part No. A0099–360, 1991, (rev. Jan. 1991).

Ph. Morin et al., "Micellar Electrokinetic Capillary Chromatography of Glucosinolates and Desulfoglucosinolates With a Cationic Surfactant," 15 Journal of High Resolution Chromatography 271 (1992).

Angela Martello, "Capillary Electrophoresis: Automating a Valuable Technique," The Scientist, vol. 4, No. 17, Sep., 3, 1990, pp. 27–28.

Wolfgang Steuer et al., "Kapillarelektrophorese," Nachrichten aus Chemie Technik und Laboratium, vol. 38, No. 5. M1–M12, And English Translation included.

Timothy Schlabach et al., "Capillary Electrophoresis of Synthetic Molecules," American Laboratory, Jun. 1991, vol. 23, No. 9,, 22–35.

Ring–Ling Chien and Dean S. Burgi, "Sample Stacking of an Extremely Large Injection Volume in High–Performance Capillary Electrophoresis," 64 Analytical Chemistry 1048 (1992).

Xiaohua Huang et al., "Quantitative Analysis of Low–Molecular Weight Carboxylic Acids by Capillary Zone Electrophoresis/Conductivity Detection," 61 Analytical Chemistry 766 (1989).

*Spectra Phoresis 1000 Software and Training Reference Manual*, Spectra Physics Analytical, part No. A0099–377, 1992 (rev. Jul. 1992).

Christiansen and Hansen, "Separation of the proteins, peptides and fragments of ADS by E.C.", Dossier Electrophorese Capillaire, 1990.

T. Schlabach, "Analyze of a tryptic digestion and artificial sweetening substances by E.C.", Dossier Electrophorese Capillaire, 1990.

$14^{th}$ International Congress of Biochemistry Abstracts vol. I, Jul. 10–11, 1988.

$14^{st}$ International Congress of Biochemistry Abstracts vol. II, Jul. 12, 1988.

$14^{st}$ International Congress of Biochemistry Abstracts vol. III, Jul. 13, 1988.

$14^{st}$ International Congress of Biochemistry Abstracts vol. IV, Jul. 14, 1988.

$14^{st}$ International Congress of Biochemistry Abstracts vol. V, Jul. 15, 1988.

The Applied Biosystems Newsletter for the Life Science Researcher, Oct. 1989.

Steven L. Petersen and Nathan E. Ballou, "Effects of Capillary Temperature Control and Electrophoretic Heterogeneity on Parameters Characterizing Separations of Particles by Capillary Zone Electrophoresis," 64 *Analytical Chemistry* 1676 (1992).

*Spectra Phoresis 1000 Gives You What's Been Missing in Capillary Electrophoresis, Spectra*, Spectra–Physics.

*Spectra Phoresis 1000 Software and Training Reference Manual*, Spectra Physics Analytical, part No. A0099–377, 1992, (rev. Jul. 1992).

Harold Swerdlow et al., "Capillary Gel Electrophoresis for DNA Sequencing, Laser–induced Fluorescence Detection with the Sheath Flow Cuvette," 516 *Journal of Chromatography* 61 (1990).

PhoresisFACTS, Issue 1, Winter 1991, Spectra–Physics, 1991.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claim 15 is confirmed.

Claims 11 and 18 are cancelled.

Claims 1–10, 12–14, 16 and 17 were not reexamined.

\* \* \* \* \*